(12) United States Patent
Osumi et al.

(10) Patent No.: US 11,786,220 B2
(45) Date of Patent: Oct. 17, 2023

(54) ULTRASOUND DIAGNOSTIC APPARATUS

(71) Applicant: Toshiba Medical Systems Corporation, Otawara (JP)

(72) Inventors: Ryota Osumi, Nasushiobara (JP); Tomohisa Imamura, Kawasaki (JP); Kuramitsu Nishihara, Otawara (JP); Hiroki Yoshiara, Saitama (JP); Hiroaki Ishikawa, Kawasaki (JP); Yuko Takada, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 503 days.

(21) Appl. No.: 15/244,384

(22) Filed: Aug. 23, 2016

(65) Prior Publication Data
US 2017/0055956 A1 Mar. 2, 2017

(30) Foreign Application Priority Data

Aug. 24, 2015 (JP) .................................. 2015-164996
Aug. 19, 2016 (JP) .................................. 2016-161271

(51) Int. Cl.
*A61B 8/08* (2006.01)
*A61B 8/06* (2006.01)
(Continued)

(52) U.S. Cl.
CPC .............. *A61B 8/5246* (2013.01); *A61B 8/06* (2013.01); *A61B 8/4416* (2013.01);
(Continued)

(58) Field of Classification Search
CPC ......... A61B 8/00; A61B 8/5223; A61B 8/485; A61B 8/5246; A61B 8/4416; A61B 8/06;
(Continued)

(56) References Cited

U.S. PATENT DOCUMENTS 5,606,971 A * 3/1997 Sarvazyan ............... A61B 8/08
600/438
5,664,571 A * 9/1997 Yamazaki ............. A61B 5/0456
600/441

(Continued)

FOREIGN PATENT DOCUMENTS

JP 2008-284287 11/2008
JP 2010-124946 A 6/2010
(Continued)

OTHER PUBLICATIONS

Japanese Office Action dated Aug. 18, 2020, issued in Japanese Patent Application No. 2016-161271.
(Continued)

*Primary Examiner* — Rochelle D Turchen
(74) *Attorney, Agent, or Firm* — Oblon, McClelland, Maier & Neustadt, L.L.P.

(57) ABSTRACT

An ultrasound diagnostic apparatus according to an embodiment includes image processing circuitry. The image processing circuitry acquires, based on a result of ultrasound scanning performed on a subject, blood flow information including a value that indicates a blood flow at each position within the subject and tissue property information including a value that indicates tissue properties at each position within the subject. The image processing circuitry generates a first image in which a difference in value in the blood flow information is represented by at least a difference in hue and a second image in which a difference in value in the tissue property information is represented by a difference other than the difference in hue. The image processing circuitry generates a combined image by combining the first image and the second image.

21 Claims, 10 Drawing Sheets

(51) Int. Cl.
*A61B 8/00* (2006.01)
*G01S 7/52* (2006.01)
*G01S 15/89* (2006.01)

(52) U.S. Cl.
CPC ........... *G01S 7/52085* (2013.01); *A61B 8/463* (2013.01); *A61B 8/485* (2013.01); *A61B 8/488* (2013.01); *A61B 8/5207* (2013.01); *A61B 8/5223* (2013.01); *G01S 7/52042* (2013.01); *G01S 15/8979* (2013.01)

(58) Field of Classification Search
CPC ... A61B 8/5207; A61B 8/463; A61B 8/13–14; A61B 8/488
See application file for complete search history.

(56) References Cited

U.S. PATENT DOCUMENTS

| | | | | |
|---|---|---|---|---|
| 5,904,652 | A * | 5/1999 | Gilbert | A61B 8/56 600/447 |
| 2005/0240101 | A1 * | 10/2005 | Kato | A61B 8/13 600/437 |
| 2007/0032726 | A1 | 2/2007 | Osaka et al. | |
| 2008/0032726 | A1 * | 2/2008 | Tajima | H04L 1/0003 455/509 |
| 2009/0018444 | A1 * | 1/2009 | Osaka | A61B 5/0048 600/437 |
| 2009/0149752 | A1 * | 6/2009 | Osaka | A61B 5/0048 600/438 |
| 2010/0041994 | A1 * | 2/2010 | Abe | A61B 8/429 600/443 |
| 2010/0130861 | A1 * | 5/2010 | Shimazaki | A61B 8/488 600/443 |
| 2012/0287156 | A1 * | 11/2012 | Tsujita | A61B 8/06 345/629 |
| 2013/0096430 | A1 * | 4/2013 | Yoshiara | A61B 8/0841 600/438 |
| 2014/0039317 | A1 * | 2/2014 | Sato | A61B 8/54 600/443 |
| 2015/0119712 | A1 * | 4/2015 | Tanigawa | G01S 7/52085 600/438 |
| 2015/0173717 | A1 * | 6/2015 | Tanigawa | A61B 8/08 600/441 |
| 2015/0272547 | A1 * | 10/2015 | Freiburger | A61B 8/485 600/438 |
| 2015/0320395 | A1 | 11/2015 | Sato | |
| 2016/0058410 | A1 * | 3/2016 | Kim | A61B 8/461 600/437 |

FOREIGN PATENT DOCUMENTS

| | | | | |
|---|---|---|---|---|
| JP | 2012-110527 | | 6/2012 | |
| JP | 2012110527 | A * | 6/2012 | ............ A61B 8/06 |
| JP | 2015-008733 | A | 1/2015 | |
| JP | 2015-104412 | A | 6/2015 | |
| JP | 2015-119819 | A | 7/2015 | |
| WO | WO 2011/099410 | A1 | 8/2011 | |

OTHER PUBLICATIONS

Japanese Office Action dated Dec. 22, 2020, issued in Japanese Patent Application No. 2016-161271.

* cited by examiner

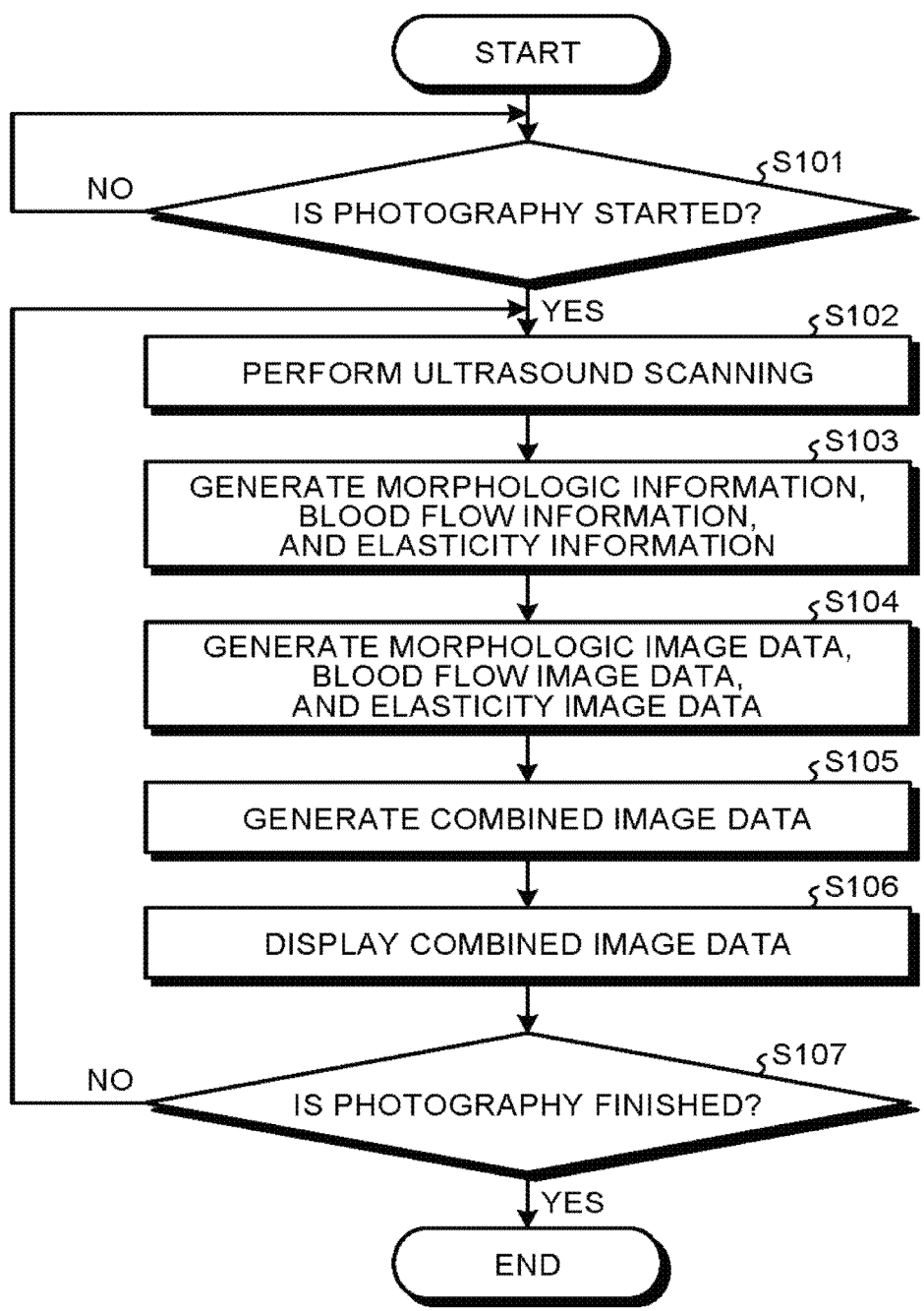

ULTRASOUND DIAGNOSTIC APPARATUS

CROSS-REFERENCE TO RELATED APPLICATIONS

This application is based upon and claims the benefit of priority from Japanese Patent Application No. 2015-164996, filed on Aug. 24, 2015; and Japanese Patent Application No. 2016-161271, filed on Aug. 19, 2016, the entire contents of which are incorporated herein by reference.

FIELD

Embodiments described herein relate generally to an ultrasound diagnostic apparatus.

BACKGROUND

Ultrasound diagnostic apparatuses are configured to irradiate the inside of a subject with an ultrasound pulse generated from ultrasound transducer elements incorporated in an ultrasound probe, and to receive waves reflected from a subject tissue by the ultrasound transducer elements, to thereby generate and display image data and any other information.

For example, Doppler imaging for imaging the flow of blood by utilizing the Doppler effect is known as an image diagnostic support method using an ultrasound diagnostic apparatus. In color Doppler imaging, which is widely used, ultrasound waves are transmitted and received a plurality of times on the same scanning line, and moving target indicator (MTI) filtering is applied to a data sequence at the same position, to thereby suppress a signal (clutter signal) derived from a static tissue or a slow-moving tissue and extract a signal derived from a blood flow. Then, in color Doppler imaging, blood flow information, such as the velocity of the blood flow, the dispersion of the blood flow, and the power of the blood flow, is estimated from the extracted blood flow signal, and a blood flow image (color Doppler image) in which the distribution of the estimated result is two-dimensionally represented in color is displayed.

Another known image diagnostic support method using an ultrasound diagnostic apparatus is, for example, elastography for measuring the tissue hardness as one of tissue properties of a biological tissue and converting the distribution of the measured hardness into an image. In elastography, stress is applied to a biological tissue by a method such as applying and releasing pressure to and from a biological tissue from the body surface with use of an ultrasound probe, and applying acoustic radiation force to a biological tissue from the body surface with use of an ultrasound probe, and information on a strain of a tissue in a living body caused by the application of the stress is generated and displayed as an elasticity image.

Note that, the above-mentioned blood flow image or elasticity image can be superimposed on or displayed side by side with a tomographic image (B-mode image) that is generated based on substantially the same cross-section as that of the blood flow image or elasticity image.

BRIEF DESCRIPTION OF THE DRAWINGS

FIG. 7 is a flowchart illustrating a processing procedure of the ultrasound diagnostic apparatus according to the first embodiment;

DETAILED DESCRIPTION

An ultrasound diagnostic apparatus according to an embodiment includes image processing circuitry. The image processing circuitry acquires, based on a result of ultrasound scanning performed on a subject, blood flow information including a value that indicates a blood flow at each position within the subject and tissue property information including a value that indicates tissue properties at each position within the subject. The image processing circuitry generates a first image in which a difference in value in the blood flow information is represented by at least a difference in hue and a second image in which a difference in value in the tissue property information is represented by a difference other than the difference in hue. The image processing circuitry generates a combined image by combining the first image and the second image.

Referring to the accompanying drawings, an ultrasound diagnostic apparatus and a medical image processing apparatus according to the embodiments are described below.

First Embodiment

Figure 1:
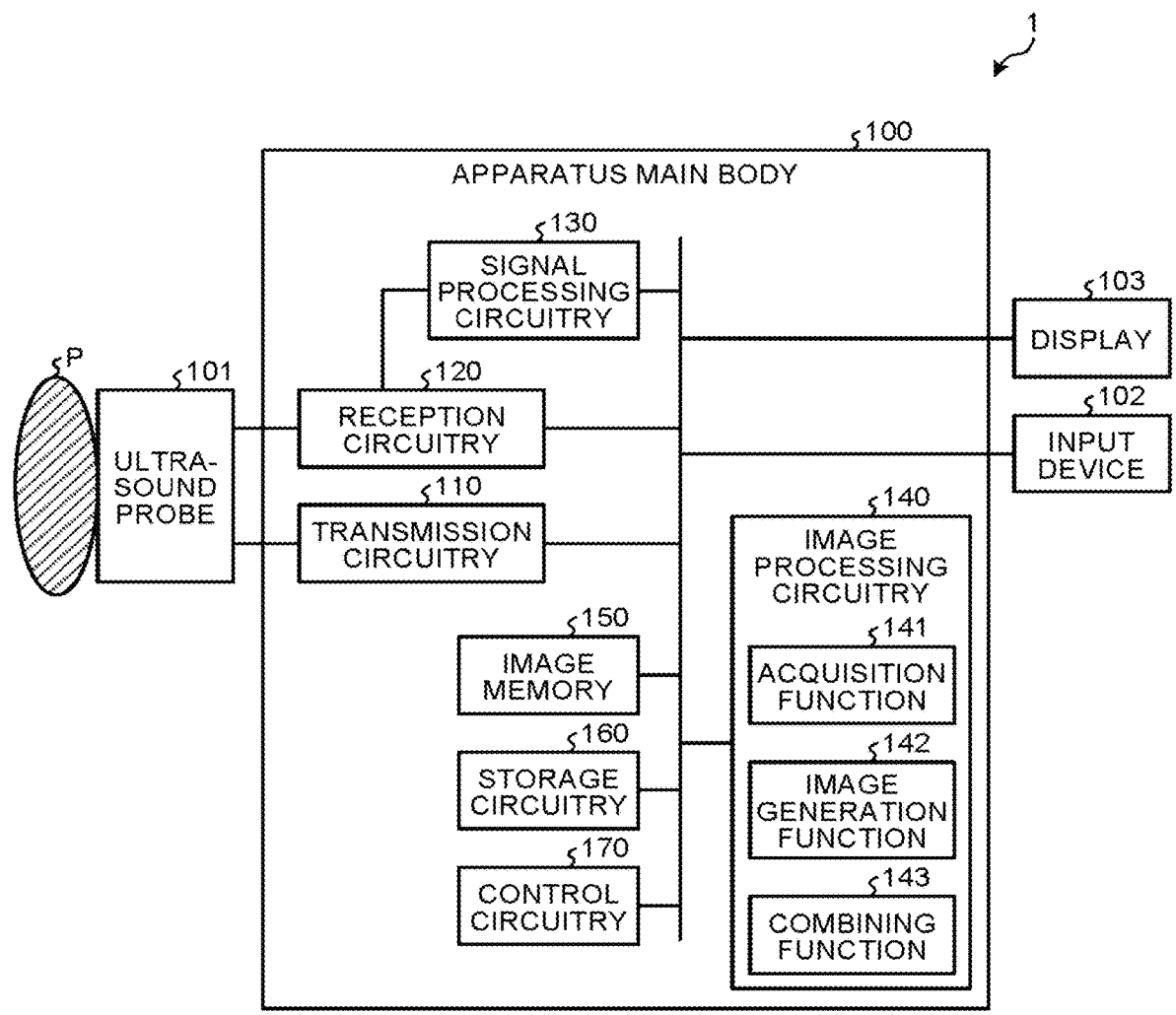
FIG. 1 is a block diagram illustrating a configuration example of an ultrasound diagnostic apparatus according to a first embodiment.

FIG. 1 is a block diagram illustrating a configuration example of an ultrasound diagnostic apparatus 1 according to a first embodiment. As illustrated in FIG. 1, the ultrasound diagnostic apparatus 1 according to the first embodiment includes an apparatus main body 100, an ultrasound probe 101, an input device 102, and a display 103. The ultrasound probe 101, the input device 102, and the display 103 are each connected to the apparatus main body 100.

The ultrasound probe 101 is brought into contact with the body surface of a subject P to transmit and receive ultrasound waves (ultrasound scanning). For example, the ultrasound probe 101 is a 1D array probe, which includes a plurality of piezoelectric transducer elements that are one-dimensionally arranged in a predetermined direction. The plurality of piezoelectric transducer elements generate ultrasound waves based on drive signals supplied from transmission circuitry 110 included in the apparatus main body 100 described later. The generated ultrasound waves are reflected by an acoustic impedance mismatch surface within the subject, and are received by the plurality of piezoelectric transducer elements as reflected wave signals that contain a component scattered by a scattering substance within a tissue and any other component. The ultrasound probe 101 transmits the reflected wave signals received by the plurality of piezoelectric transducer elements to the transmission circuitry 110.

Note that, the case where a 1D array probe is used as the ultrasound probe 101 is described in this embodiment, but the ultrasound probe 101 is not limited thereto. Any type of ultrasound probe may be used as the ultrasound probe 101, such as a 2D array probe in which a plurality of piezoelectric transducer elements are two-dimensionally arranged in a grid, and a mechanical 4D probe in which a plurality of piezoelectric transducer elements are one-dimensionally arranged and mechanically oscillated to scan a three-dimensional region.

The input device 102 includes a mouse, a keyboard, a button, a panel switch, a touch command screen, a foot switch, a trackball, or a joystick. The input device 102 receives various kinds of setting requests from an operator of the ultrasound diagnostic apparatus 1, and transfers various kinds of received setting requests to the apparatus main body 100.

The display 103 displays a graphical user interface (GUI) used for the operator of the ultrasound diagnostic apparatus 1 to input various kinds of setting requests with the input device 102, and displays ultrasound image data generated in the apparatus main body 100 and any other data.

The apparatus main body 100 is an apparatus configured to generate ultrasound image data based on reflected wave signals received by the ultrasound probe 101. As illustrated in FIG. 1, the apparatus main body 100 includes, for example, the transmission circuitry 110, reception circuitry 120, signal processing circuitry 130, image processing circuitry 140, image memory 150, storage circuitry 160, and control circuitry 170. The transmission circuitry 110, the signal processing circuitry 130, the image processing circuitry 140, the image memory 150, the storage circuitry 160, and the control circuitry 170 are communicably connected to one another.

The transmission circuitry 110 controls the transmission of ultrasound waves from the ultrasound probe 101. For example, based on an instruction from the control circuitry 170 described later, the transmission circuitry 110 applies drive signals (drive pulses) to the ultrasound probe 101 at timings delayed for predetermined transmission delay times set for the respective transducer elements. In this manner, the transmission circuitry 110 controls the ultrasound probe 101 to transmit an ultrasound beam in which ultrasound waves are focused in a beam.

The reception circuitry 120 controls the reception of reflected wave signals obtained when the transmitted ultrasound waves are reflected by a body tissue. For example, based on an instruction from the control circuitry 170 described later, the reception circuitry 120 performs addition processing by adding predetermined delay times to the reflected wave signals received by the ultrasound probe 101. In this manner, a reflected component of the reflected wave signals from the direction of reception directivity is emphasized. Then, the reception circuitry 120 converts the reflected wave signals subjected to the addition processing into an in-phase signal (I signal) and a quadrature-phase signal (Q signal) in a baseband bandwidth. Then, the reception circuitry 120 transmits the I signal and the Q signal (hereinafter referred to as "IQ signals") to the signal processing circuitry 130 as reflected wave data. Note that, the reception circuitry 120 may convert the reflected wave signals subjected to the addition processing into a radio frequency (RF) signal and then transmit the resultant signal to the signal processing circuitry 130. The IQ signals and the RF signal are signals containing phase information (reflected wave data).

The signal processing circuitry 130 performs various kinds of signal processing on the reflected wave data, which is generated by the reception circuitry 120 from the reflected wave signals. For example, the signal processing circuitry 130 performs processing described below to generate morphologic information that is based on the morphology of a structure within the subject, blood flow information that is based on the blood flow within the subject, and elasticity information that is based on the tissue elasticity within the subject.

Figure 2:
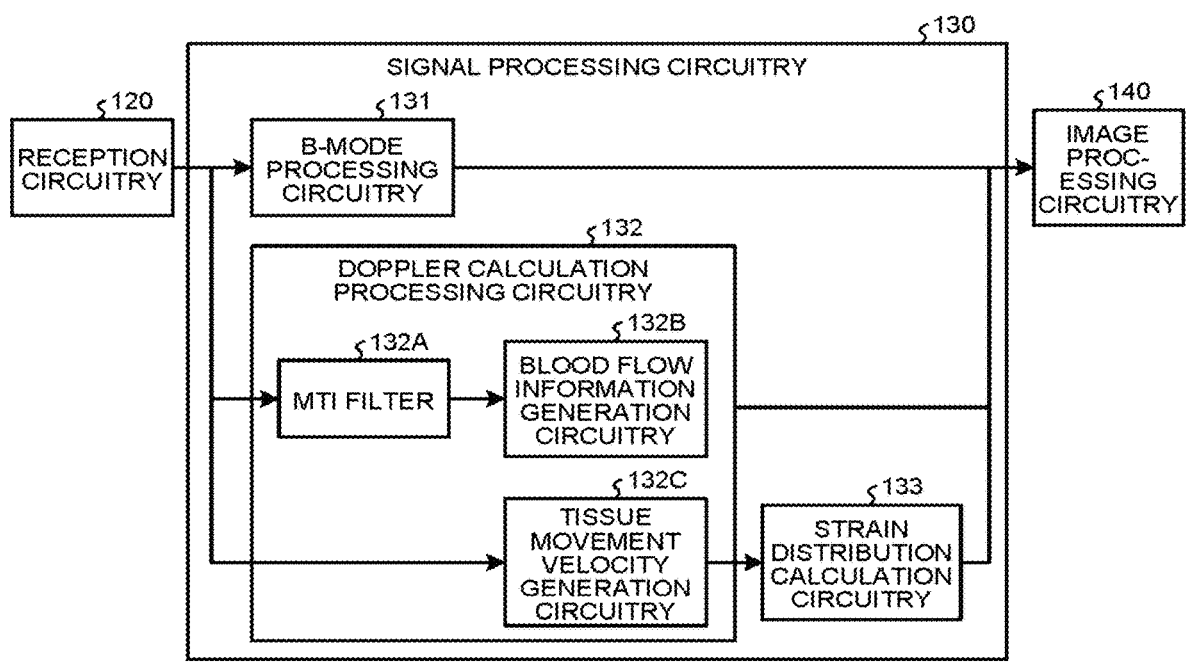
FIG. 2 is a block diagram illustrating a configuration example of a signal processing circuit according to the first embodiment.

FIG. 2 is a block diagram illustrating a configuration example of the signal processing circuitry 130 according to the first embodiment. As illustrated in FIG. 2, the signal processing circuitry 130 includes B-mode processing circuitry 131, Doppler calculation processing circuitry 132, and strain distribution calculation circuitry 133.

The B-mode processing circuitry 131 performs logarithmic amplification, envelope detection, and any other processing on the reflected wave data, to thereby generate data (B-mode data) in which signal intensities at a plurality of sample points (observation points) are each represented by the level of luminance. The B-mode processing circuitry 131 transmits the generated B-mode data to the image processing circuitry 140. Note that, the B-mode data is an example of tomographic information and morphologic information.

The Doppler calculation processing circuitry 132 performs frequency analysis on velocity information from the reflected wave data, to thereby generate data (Doppler data) in which motion information on a moving body within a scanning range based on the Doppler effect is extracted for each sample point. Specifically, the Doppler calculation processing circuitry 132 generates Doppler data in which an average velocity, a variance, a power value, and any other parameter are extracted at each of a plurality of sample points as motion information of a moving body. The moving body as used herein refers to, for example, a blood flow, a tissue such as the wall of the heart, and a contrast agent. The Doppler calculation processing circuitry 132 according to this embodiment generates information in which an average velocity of the blood flow, an average variance of the blood flow, an average power value of the blood flow, and any other parameter are estimated at each of a plurality of sample points as motion information on the blood flow (blood flow information). In other words, the blood flow information is information including a value that is based on the blood flow at each sample point (value representing blood flow).

As illustrated in FIG. 2, the Doppler calculation processing circuitry 132 includes the moving target indicator (MTI) filter 132A, blood flow information generation circuitry 132B, and tissue movement velocity generation circuitry 132C.

The MTI filter 132A and the blood flow information generation circuitry 132B calculate blood flow information by color Doppler imaging. In color Doppler imaging, ultrasound waves are transmitted and received a plurality of times on the same scanning line, and the MTI filter 132A is applied to a data sequence at the same position, to thereby suppress a signal (clutter signal) derived from a static tissue or a slow-moving tissue and extract a signal derived from the blood flow. Then, in color Doppler imaging, blood flow information, such as the velocity of the blood flow, the dispersion of the blood flow, and the power of the blood flow, is estimated based on the extracted blood flow signal.

Specifically, the MTI filter 132A uses a filter matrix to output a data sequence in which a clutter component is suppressed and a blood flow signal derived from the blood flow is extracted from a data sequence of continuous reflected wave data at the same position (same sample point). The blood flow information generation circuitry 132B estimates blood flow information by performing self-correlation calculation using the data output from the MTI filter 132A and any other calculation, and outputs the estimated blood flow information.

Note that, examples of filters applicable to the MTI filter 132A include filters with fixed coefficients, such as a Butterworth infinite impulse response (IIR) filter and a polynomial regression filter, and an adaptive filter whose coefficient is changed depending on an input signal with use of eigenvectors or the like.

In order to generate elasticity information representing the elasticity of a tissue, the tissue movement velocity generation circuitry 132C executes tissue Doppler imaging (TDI) for displaying the spatial distribution of information on the motion of the tissue. In TDI, ultrasound waves are transmitted and received a plurality of times on the same scanning line similarly to the above-mentioned color Doppler imaging. The TDI, however, differs from the color Doppler imaging in that a phase difference of the above-mentioned data sequence and tissue movement velocity are calculated without applying the MTI filter 132A. The generated tissue movement velocity information is converted by the strain distribution calculation circuitry 133 into elasticity information representing the elasticity of the tissue.

Specifically, the tissue movement velocity generation circuitry 132C performs self-correlation calculation and any other calculation on a data sequence of continuous reflected wave data at the same position (without applying MTI filter 132A), and outputs tissue movement velocity information representing the movement velocity of the tissue (tissue motion information). Then, based on the tissue movement velocity information, the strain distribution calculation circuitry 133 calculates a displacement of the tissue by time integration of the movement velocity of the tissue after the tissue starts to deform, and further takes the spatial derivative of the displacement, to thereby calculate strain data representing the strain of the tissue as elasticity information. Note that, the case where TDI is performed to generate the elasticity information is described above, but the generation method is not limited thereto. For example, in TDI, the generated tissue movement velocity information itself may be output in order to image the spatial distribution of the tissue movement velocities. The elasticity information is an example of tissue property information including a value that is based on a tissue property (hardness) (value representing tissue property) at each position within the subject. The MTI filter 132A is an example of a clutter removal filter.

As described above, the signal processing circuitry 130 subjects the reflected wave data to various kinds of signal processing by the B-mode processing circuitry 131, the Doppler calculation processing circuitry 132, and the strain distribution calculation circuitry 133, to thereby generate morphologic information, blood flow information, and elasticity information. Specifically, the signal processing circuitry 130 applies clutter removal filtering for removing a clutter component to a received data sequence obtained by a plurality of times of ultrasound wave transmission and reception at the same position, and acquires blood flow information from the received data sequence after the application of the clutter removal filtering. Furthermore, the signal processing circuitry 130 acquires tissue property information from the received data sequence before the application of the clutter removal filtering. The tissue property information is acquired based on correlation calculation between a plurality of received data pieces including the received data used for the acquisition of the blood flow information.

Note that, FIG. 2 is only illustrative. For example, a blood flow signal removal filter for removing a signal derived from the blood flow may be arranged at a preceding stage of the tissue movement velocity generation circuitry 132C. Specifically, the tissue movement velocity generation circuitry 132C applies blood flow signal removal filtering to a data sequence of reflected wave data, and generates tissue movement velocity information from the data sequence after the application of the blood flow signal removal filtering. Note that, the blood flow signal removal filter is, for example, a low pass filter configured to remove a frequency component corresponding to a blood flow signal.

Furthermore, the signal processing circuitry 130 according to the first embodiment performs color Doppler imaging and TDI on the result of the same ultrasound scanning, to thereby generate blood flow information and elasticity information from the same data sequence.

Figure 3:
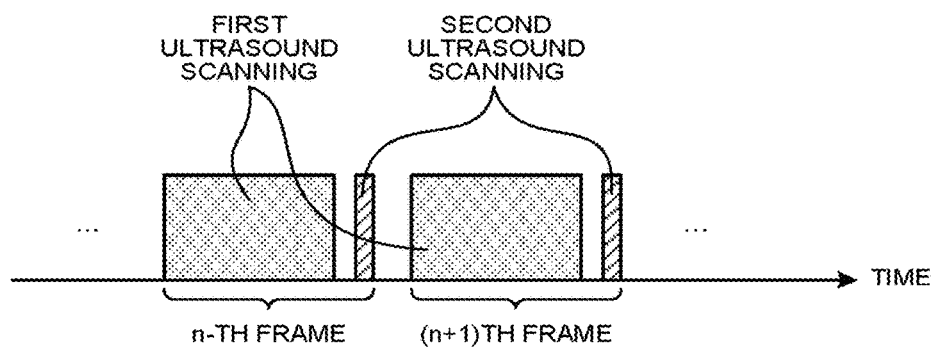
FIG. 3 is a diagram illustrating an exemplary scan sequence according to the first embodiment.

FIG. 3 is a diagram illustrating an exemplary scan sequence according to the first embodiment. In FIG. 3, the horizontal axis corresponds to time. Ultrasound scanning for each frame includes first ultrasound scanning and second ultrasound scanning.

As illustrated in FIG. 3, the first ultrasound scanning and the second ultrasound scanning are performed in each frame. The first ultrasound scanning is scanning in which ultrasound waves are transmitted and received a plurality of times (number of ensembles) on the same scanning line. The signal processing circuitry 130 performs color Doppler imaging and TDI on the result of the first ultrasound scanning, to thereby generate blood flow information and elasticity information from the same data sequence. Specifically, the signal processing circuitry 130 applies the MTI filter 132A to a data sequence of reflected wave data obtained by the first ultrasound scanning for the n-th frame, and performs self-correlation calculation and any other calculation to generate blood flow information. Furthermore, the signal processing circuitry 130 performs self-correlation calculation and any other calculation on the data sequence of the reflected wave data obtained by the first ultrasound scanning for the n-th frame without applying the MTI filter 132A, to thereby generate tissue movement velocity information. The second ultrasound scanning is scanning in which ultrasound waves are transmitted and received once for each scanning line. The signal processing circuitry 130 generates morphologic information based on the result of the second ultrasound scanning.

As described above, the signal processing circuitry 130 generates the blood flow information and the elasticity information based on the result of the same ultrasound scanning. Note that, in the first embodiment, the reason why the blood flow information and the elasticity information are generated from the result of the same ultrasound scanning is that the reflected wave data that contains a small amount of clutter signals and that is capable of generating tissue strain information is collected. Specifically, even when the operator does not actively oscillate the ultrasound probe 101, the strain information can be generated based on minute vibration that occurs due to the action of bringing the ultrasound probe 101 into contact with the body surface. Therefore, reflected wave data that is collected when the ultrasound probe 101 is not actively oscillated contains the strain information and a small amount of clutter signals derived from oscillation, and hence the blood flow information and the elasticity information can be generated from the same data sequence.

Note that, FIG. 3 is only illustrative. For example, the second ultrasound scanning is not necessarily required to be performed after the first ultrasound scanning. Furthermore, for example, blood flow information and elasticity information are not necessarily required to be generated from the result of the same ultrasound scanning.

The description returns to FIG. 1. The image processing circuitry 140 performs processing of generating image data (ultrasound image data), various kinds of image processing for the image data, and any other processing. For example, the image processing circuitry 140 converts a scanning mode of the B-mode data (morphologic information), blood flow information, and elasticity information generated by the signal processing circuitry 130 into a display data format (scan conversion). In this manner, the image processing circuitry 140 generates each of B-mode image data (morphologic image data) representing the morphology of a structure of the subject, blood flow image data representing the motion of the blood flow within the subject, and elasticity image data representing the tissue elasticity within the subject. The image processing circuitry 140 stores the generated image data and the image data subjected to various kinds of image processing in the image memory 150. Note that, the image processing circuitry 140 may also generate, together with the image data, information indicating a display position of each image data, various kinds of information for assisting the operation of the ultrasound diagnostic apparatus, and supplementary information on diagnosis, such as patient information, and store these pieces of information in the image memory 150.

The image processing circuitry 140 according to the first embodiment executes an acquisition function 141, an image generation function 142, and a combining function 143. Respective processing functions to be executed by the acquisition function 141, the image generation function 142, and the combining function 143, which are the components of the control circuitry 170, are recorded in the storage circuitry 160 in the form of programs that can be executed by a computer, for example. The image processing circuitry 140 is a processor configured to read each program from the storage circuitry 160 and execute the program to implement the function corresponding to the program. Specifically, the acquisition function 141 is a function to be implemented when the image processing circuitry 140 reads the program corresponding to the acquisition function 141 from the storage circuitry 160 and executes the program. The image generation function 142 is a function to be implemented when the image processing circuitry 140 reads the program corresponding to the image generation function 142 from the storage circuitry 160 and executes the program. The combining function 143 is a function to be implemented when the image processing circuitry 140 reads the program corresponding to the combining function 143 from the storage circuitry 160 and executes the program. In other words, the image processing circuitry 140 that has read each program has each function illustrated in the image processing circuitry 140 in FIG. 1. Each of the acquisition function 141, the image generation function 142, and the combining function 143 is described later.

Note that, in FIG. 1, a description is given of the case where the processing functions executed by the acquisition function 141, the image generation function 142, and the combining function 143 are implemented by the single image processing circuitry 140. However, a processing circuit may be formed by a combination of a plurality of independent processors, and the functions may be implemented by each processor executing a program.

The term "processor" used in the above description means, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor implements its functions by reading and executing the programs stored in the storage circuit. Note that, a program may be directly incorporated in a circuit of the processor instead of storing a program in the storage circuitry 160. In this case, the processor implements its functions by reading and executing the programs incorporated in the circuit. Note that, each processor in this embodiment is not limited to the case where each processor is configured as a single circuit, and a plurality of independent circuits may be combined to configure a single processor so as to implement their functions. In addition, the plurality of components in FIG. 1 may be integrated into a single processor so as to implement their functions.

The image memory 150 is a memory configured to store the image data (such as B-mode image data, blood flow image data, and elasticity image data) generated by the image processing circuitry 140. Furthermore, the image memory 150 is capable of storing data generated by the signal processing circuitry 130. The B-mode data, blood flow information, and elasticity information stored in the image memory 150 can be invoked by the operator after diagnosis, for example, and serve as display ultrasound image data via the image processing circuitry 140.

The storage circuitry 160 stores control programs for executing ultrasound transmission and reception, image processing, and display processing, diagnosis information (for example, patient IDs and doctor's findings), and various kinds of data such as diagnosis protocols and various kinds of body marks. If necessary, the storage circuitry 160 is also used to store image data stored in the image memory 150. Furthermore, the data stored in the storage circuitry 160 can be transferred to an external device via an interface unit (not shown).

The control circuitry 170 controls the overall processing of the ultrasound diagnostic apparatus 1. Specifically, the control circuitry 170 controls the processing of the transmission circuitry 110, the reception circuitry 120, the signal processing circuitry 130, the image processing circuitry 140, and any other circuit based on various kinds of setting requests input by the operator via the input device 102 and various kinds of control programs and various kinds of data read from the storage circuitry 160. Furthermore, the control circuitry 170 displays the ultrasound image data stored in the image memory 150 on the display 103.

Note that, the transmission circuitry 110, the reception circuitry 120, the signal processing circuitry 130, the image processing circuitry 140, the control circuitry 170, and any other circuit built in the apparatus main body 100 may be configured by hardware as represented by a processor (such as a central processing unit (CPU), a micro-processing unit (MPU), and an integrated circuit), but may be configured by programs in the form of software modules.

By the way, it is a common practice to combine a blood flow image or an elasticity image with a B-mode image having a positional correspondence therewith for display. Specifically, the blood flow image or the elasticity image is superimposed on the B-mode image at a corresponding position to improve visibility. This contributes to an improvement in diagnosis accuracy and a reduction in diagnosis time.

Simply combining the images, however, does not always improve visibility. For example, the blood flow image and the elasticity image are generally displayed in color, and hence the two superimposed images may reduce visibility. Specifically, the blood flow image is colored with "red-blue" depending on the direction of the blood flow. The elasticity image, on the other hand, is colored with gradation that continuously changes in the order of "blue-green-red" depending on the level (magnitude) of strain. Therefore, if the blood flow image and the elasticity image are superimposed on each other with a predetermined transparency, for example, it cannot be distinguished whether a "red" pixel indicates the direction of the blood flow or the level of strain, thus leading to a reduction in visibility. Such a reduction in visibility cannot be solved by adjustment of transparencies of the images or division of imaged regions.

To address this problem, the ultrasound diagnostic apparatus 1 according to the first embodiment has the configuration disclosed herein in order to generate a combined image in which a blood flow and a tissue property are appropriately represented.

The acquisition function 141 acquires B-mode data (morphologic information), blood flow information, and elasticity information based on a result of ultrasound scanning performed on a subject. For example, the acquisition function 141 acquires B-mode data, blood flow information, and elasticity information generated by the signal processing circuitry 130. Then, the acquisition function 141 transmits the acquired B-mode data, blood flow information, and elasticity information to the image generation function 142. Note that, the acquisition function 141 is an example of an acquisition unit. The elasticity information is an example of tissue property information.

Note that, the case where the acquisition function 141 acquires B-mode data, blood flow information, and elasticity information is described above, but the embodiments are not limited thereto. For example, the acquisition function 141 may acquire information (for example, supplementary information) other than the above-mentioned pieces of information. Furthermore, for example, the acquisition function 141 is not necessarily required to acquire the above-mentioned pieces of information. For example, when no B-mode data is used in the following processing, B-mode data may not be acquired. In this case, the acquisition function 141 acquires blood flow information and elasticity information from the signal processing circuitry 130.

The image generation function 142 generates, based on the result of ultrasound scanning performed on the subject P, each of a B-mode image that represents the morphology of a structure within the subject, a blood flow image in which a difference in value in the blood flow information is represented by a difference in hue, and an elasticity image in which a difference in value in the elasticity information is represented by the gray scale. Note that, the image generation function 142 is an example of an image generation unit.

Figure 4A:
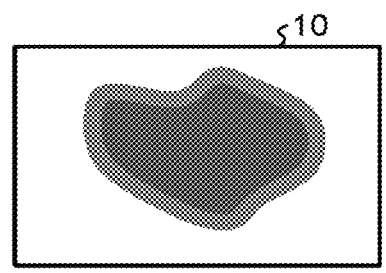
FIG. 4A is a diagram for describing processing of an image generation function according to the first embodiment.
Figure 4B:
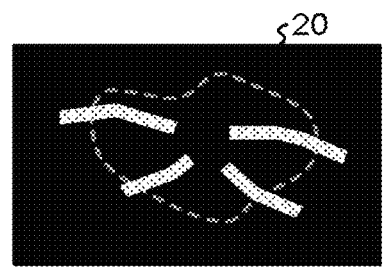
FIG. 4B is a diagram for describing processing of the image generation function according to the first embodiment.

FIG. 4A and FIG. 4B are diagrams for describing processing of the image generation function 142 according to the first embodiment. FIG. 4A exemplifies an elasticity image 10 generated by the image generation function 142. FIG. 4B exemplifies a blood flow image 20 generated by the image generation function 142. Note that, the broken line in FIG. 4B shows the positional correspondence with the elasticity image 10 of FIG. 4A, and is not displayed on the blood flow image 20 in practice.

As illustrated in FIG. 4A, for example, the image generation function 142 converts a scanning mode of the elasticity information generated by the signal processing circuitry 130 into a display data format. The converted data is data in which a value in the elasticity information representing the strain of a tissue at each sample point is replaced with a pixel value of each pixel of the display image. Then, the image generation function 142 allocates each pixel in the converted data with a color corresponding to its pixel value in accordance with an elasticity image color look-up table (LUT). In the elasticity image color LUT, gray scale colors corresponding to pixel values are set. In other words, the image generation function 142 represents a difference in pixel value in the elasticity image by the gray scale. As an example, the image generation function 142 allocates a hard region (region with small strain) with dark gray and a soft region (region with large strain) with bright gray, to thereby generate the elasticity image 10.

Note that, FIG. 4A is only illustrative. For example, the elasticity image 10 may be represented by a color LUT in which a monochrome color is allocated instead of the gray scale. In other words, the elasticity image 10 is represented by an element other than hue among the three color elements (hue, lightness, and chroma). Specifically, a difference in value in the elasticity image 10 is represented by any one of a difference in lightness, a difference in chroma, and a combination of a difference in lightness and a difference in chroma. Note that, in the case where the elasticity image 10 is represented in monochrome color, it is preferred in view of visibility that the elasticity image 10 be represented by a color different from the hue of the blood flow image 20 described later, for example, a color separated in color space from the color of the blood flow image 20.

Furthermore, as illustrated in FIG. 4B, the image generation function 142 converts a scanning mode of the blood flow information generated by the signal processing circuitry 130 into a display data format. The converted data is data in which a value in the blood flow information representing the blood flow at each sample point is replaced with a pixel value of each pixel of the display image. Then, the image generation function 142 allocates each pixel in the converted data with a color corresponding to its pixel value in accordance with a blood flow image color LUT. In the blood flow image color LUT, colors including hues (color temperatures) that differ depending on pixel values are set. Specifically, the image generation function 142 represents a difference in pixel value in the blood flow image by hue. As an example, when the power of the blood flow is imaged as blood flow information, the image generation function 142 allocates dark red to a region having high power and bright red to a region having low power, to thereby generate the blood flow image 20.

Note that, FIG. 4B is only illustrative. For example, the blood flow image 20 may be represented by hue other than red. Furthermore, the blood flow image 20 may be represented in red color and blue color depending on the directions of the blood flow, and in addition, when a velocity component and a variance component of the blood flow are displayed, the blood flow image 20 may be represented by a two-dimensional color change with use of two different color components. In other words, the blood flow image 20 is represented by at least a difference in hue among the three color elements (hue, lightness, and chroma). Specifically, the difference in value in the blood flow image 20 is represented by any one of a difference in hue, a combination of a difference in hue and a difference in lightness, a combination of a difference in hue and a difference in chroma, and a combination of a difference in hue, a difference in lightness, and a difference in chroma.

As described above, the image generation function 142 generates the blood flow image 20, in which a difference in value in the blood flow information is represented by at least a difference in hue, and the elasticity image 10, in which a difference in value in the elasticity information is represented by a difference other than the difference in hue.

The combining function 143 generates a combined image by combining the blood flow image 20 and the elasticity image 10. For example, the combining function 143 generates a combined image by superimposing the blood flow image 20 on the elasticity image 10 at a corresponding position. Note that, the combining function 143 is an example of a combining unit.

Figure 5:
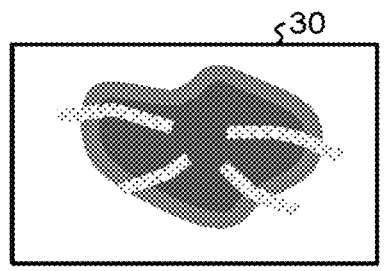
FIG. 5 is a diagram for describing processing of a combining function according to the first embodiment.
Figure 6:
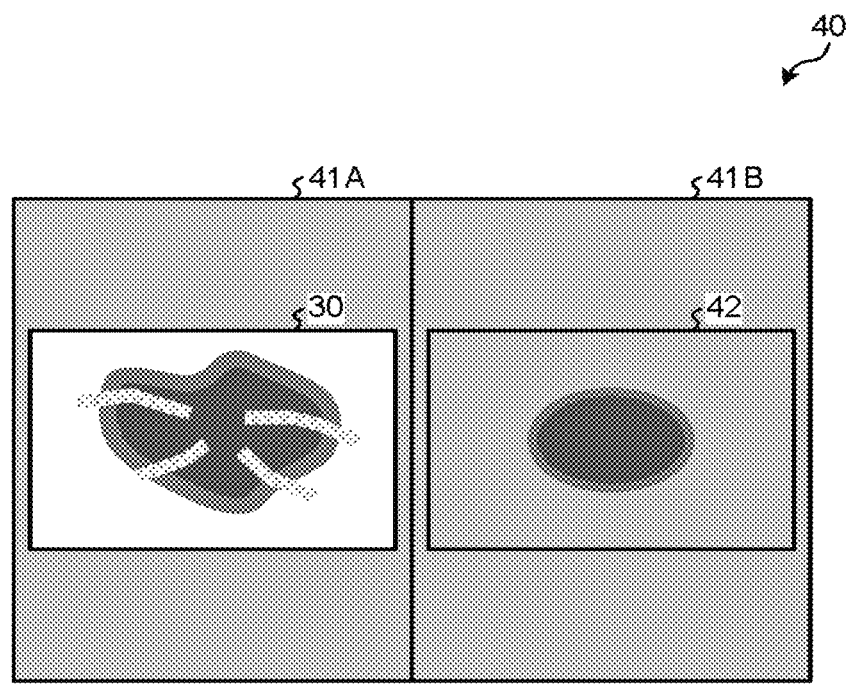
FIG. 6 is a diagram for describing processing of the combining function according to the first embodiment.

FIG. 5 and FIG. 6 are diagrams for describing processing of the combining function 143 according to the first embodiment. FIG. 5 exemplifies a combined image 30 obtained by combining the elasticity image 10 of FIG. 4A and the blood flow image 20 of FIG. 4B. FIG. 6 exemplifies a display image 40 generated with use of the combined image 30.

As illustrated in FIG. 5, the combining function 143 generates the combined image 30 by superimposing the blood flow image 20 on the elasticity image 10. Here, the elasticity image 10 and the blood flow image 20 are image data generated from the result of the same ultrasound scanning, and hence the positions of sample points (pixels) in both the image data correspond to each other. In other words, the combining function 143 superimposes the blood flow image 20 on the elasticity image 10 at the corresponding position without performing positional alignment between both the image data.

Specifically, the combining function 143 extracts a blood flow region from the blood flow image 20. For example, the combining function 143 recognizes a region in the blood flow image 20 that has Doppler information (for example, region having power value equal to or larger than threshold value) as a blood flow region, and clips out an image of the recognized blood flow region. In the example of FIG. 4B, the combining function 143 clips out four shaded regions as blood flow regions. Then, the combining function 143 generate the combined image 30 by superimposing the images of the clipped blood flow regions on the elasticity image 10 at the corresponding positions. Note that, the images of the blood flow regions superimposed at this time may be transparent with a predetermined transparency. In the example of FIG. 5, the case of using a power image as an example of the blood flow image 20 is described, but the blood flow image 20 is not limited thereto. For example, a velocity image or a dispersion image may be used.

As illustrated in FIG. 6, the combining function 143 combines the combined image 30 and B-mode images 41A and 41B, to thereby generate the display image 40 to be displayed on the display 103. Specifically, the display image 40 is divided into left and right regions in which the B-mode images 41A and 41B, which are the same tomographic images, are displayed.

Specifically, the combining function 143 superimposes the combined image 30 on the B-mode image 41A at the corresponding position in a non-transparent manner. This position is determined based on, for example, the respective sample point positions in the first ultrasound scanning and the second ultrasound scanning. In this manner, the combined image 30 is superimposed on the B-mode image 41A in a non-transparent manner, and hence luminance components of the B-mode image 41A can be prevented from being mixed in the region of the combined image 30 to reduce visibility.

Furthermore, the combining function 143 displays the B-mode image 41B, which is the same as the B-mode image 41A, side by side at the position adjacent to the B-mode image 41A having the combined image 30 superimposed thereon. The combining function 143 displays a border line 42 corresponding to the range of the combined image 30 on the B-mode image 41B. The display of the border line 42 enables the appearance of the B-mode image (tomographic image) corresponding to the range of the combined image 30 to be easily viewed, thus facilitating a comparative observation of the combined image 30 and the B-mode image 41B.

In this manner, the combining function 143 generates the display image 40. The display image 40 generated by the combining function 143 is displayed on the display 103 by the control circuitry 170.

Note that, FIG. 6 is only illustrative. For example, FIG. 6 exemplifies the case where another image is not superimposed on the B-mode image 41B, but the embodiments are not limited thereto. For example, the elasticity image 10 or the blood flow image 20 may be superimposed on the B-mode image 41B at the corresponding position with a predetermined transparency. Furthermore, for example, the combining function 143 may output the combined image 30 itself as the display image 40, and may output an image obtained by superimposing the combined image 30 on the B-mode image 41A in a non-transparent manner as the display image 40. Furthermore, for example, the combining function 143 may display an image obtained by arranging the B-mode image 41B at the position adjacent to the combined image 30 as the display image 40. In other words, the display image 40 includes at least the combined image 30 and can be generated by an appropriate combination with another image having the positional correspondence.

For example, in FIG. 6, the case of displaying the two B-mode images 41A and 41B side by side in the horizontal direction is described, but in addition thereto, the two images can be displayed side by side in various forms, such as being displayed side by side in the vertical direction, being displayed side by side with different sizes, and being displayed at the same time on different display devices. Furthermore, the number of images to be displayed side by side may be three or more. When three images are displayed side by side, two images out of the three images are set as B-mode images 41A and the other one image is set as a B-mode image 41B. The combined image 30 may be superimposed on the B-mode image 41B rather than being superimposed on the B-mode image 41A.

FIG. 7 is a flowchart illustrating a processing procedure of the ultrasound diagnostic apparatus 1 according to the first embodiment. The processing procedure illustrated in FIG. 7 is started, for example, when an instruction to start photographing a combined image 30 is received from the operator under the state in which the ultrasound probe 101 is brought into contact with the body surface of the subject P.

In Step S101, the ultrasound diagnostic apparatus 1 starts photography. For example, when the control circuitry 170 receives an instruction to start photographing the combined image 30 from the operator, the control circuitry 170 starts photographing the combined image 30. Note that, when the determination in Step S101 is negative, the control circuitry 170 remains in a standby state without starting photography.

When the determination in Step S101 is positive, in Step S102, the ultrasound probe 101 performs ultrasound scanning on the subject P. For example, the ultrasound probe 101 performs first ultrasound scanning and second ultrasound scanning for each frame (see FIG. 3).

In Step S103, the signal processing circuitry 130 generates morphologic information, blood flow information, and elasticity information. For example, the B-mode processing circuitry 131 performs logarithmic amplification, envelope detection, and any other processing on reflected wave data collected by the second ultrasound scanning, to thereby generate B-mode data. The Doppler calculation processing circuitry 132 applies clutter removal filtering to a received data sequence collected by the first ultrasound scanning, to thereby generate blood flow information from the received data sequence. Based on tissue movement velocity information acquired from the received data sequence before the application of the clutter removal filtering, the strain distribution calculation circuitry 133 calculates a displacement of the tissue by time integration of the movement velocity of the tissue after the tissue starts to deform, and further takes the spatial derivative of the displacement, to thereby generate elasticity information.

In Step S104, the image processing circuitry 140 generates morphologic image data, blood flow image data, and elasticity image data. For example, the acquisition function 141 acquires the B-mode data, blood flow information, and elasticity information generated by the signal processing circuitry 130. Then, the image generation function 142 converts a scanning mode of the B-mode data, blood flow information, and elasticity information acquired by the acquisition function 141 into a display data format (scan conversion), to thereby generate each of B-mode image data, blood flow image data, and elasticity image data. Note that, the blood flow image data generated in Step S104 is data in which a difference in value in the blood flow information is represented by at least a difference in hue, and the elasticity image data is represented by the gray scale.

In Step S105, the combining function 143 generates combined image data. For example, the combining function 143 generates the combined image 30 by superimposing the blood flow image 20 on the elasticity image 10 at the corresponding position. Then, the combining function 143 combines the display image 40 including the generated combined image 30 (see FIG. 6).

In Step S106, the control circuitry 170 displays the combined image data generated by the image processing circuitry 140 on the display 103. For example, the control circuitry 170 displays the display image 40 including the combined image 30 illustrated in FIG. 6 on the display 103.

In Step S107, the control circuitry 170 determines whether an instruction to finish photography is received from the operator. When the determination in Step S107 is negative, the control circuitry 170 proceeds to the processing of Step S102. Specifically, the ultrasound diagnostic apparatus 1 performs ultrasound scanning for the next frame, and generates and displays a combined image 30 of the next frame.

When the determination in Step S107 is positive, the ultrasound diagnostic apparatus 1 finishes the processing for generating and displaying the combined image 30. Note that, FIG. 7 is only illustrative. For example, the above-mentioned processing procedure is not necessarily required to be executed in the above-mentioned order. For example, the execution order of Steps S101 to S107 may be appropriately changed unless the processing contents are contradictory.

As described above, in the ultrasound diagnostic apparatus 1 according to the first embodiment, the acquisition function 141 acquires blood flow information and tissue property information based on the result of ultrasound scanning performed on a subject. The image generation function 142 generates a blood flow image in which a difference in value in the blood flow information is represented by at least a difference in hue and a tissue property image in which a difference in value in the tissue property information is represented by a difference other than the difference in hue. The combining function 143 generates a combined image by combining the blood flow image and the tissue property image. Consequently, the ultrasound diagnostic apparatus 1 according to the first embodiment can generate a combined image in which the blood flow and the tissue property are appropriately represented.

For example, the ultrasound diagnostic apparatus 1 acquires the elasticity image 10 and the blood flow image 20 from the same ultrasound scanning, that is, the same cross-section. Consequently, the ultrasound diagnostic apparatus 1 can accurately superimpose the two images, and hence an improvement in diagnosis accuracy is expected. In some medical specialties and in some types of examination, the elasticity image 10 and the blood flow image 20 are used together in many cases, and hence the ultrasound diagnostic apparatus 1 is useful particularly in these cases.

Furthermore, the ultrasound diagnostic apparatus 1 reduces the number of times of ultrasound scanning to be executed in each frame, and hence the frame rate improves. Furthermore, the ultrasound diagnostic apparatus 1 eliminates the need of switching photographing modes for independently collecting the elasticity image 10 and the blood flow image 20, with the result that the diagnosis time can be reduced.

Furthermore, in the ultrasound diagnostic apparatus 1, the image generation function 142 generates a morphologic image, a blood flow image, and a tissue property image based on the result of ultrasound scanning performed on a subject. Then, the control circuitry 170 displays a display image that includes the combined image 30 in which the blood flow image and the tissue property image are combined and a display image that includes the morphologic image 41B on the display 103 so that the display images are displayed side by side. Consequently, the ultrasound diagnostic apparatus 1 allows the operator to view the morphologic image, the blood flow image, and the tissue property image at the same time without impairing visibility.

Second Embodiment

In the first embodiment, the case of combining the blood flow image 20 and the elasticity image 10 in such a manner that the blood flow image 20 drawn by hue and the elasticity image 10 drawn by monochrome color gradation (for example, grayscale) is described, but the embodiments are not limited thereto. For example, the ultrasound diagnostic apparatus 1 may combine a blood flow image drawn by monochrome color gradation and an elasticity image drawn by hue. In a second embodiment, the case where the ultrasound diagnostic apparatus 1 combines a blood flow image drawn by monochrome color gradation and an elasticity image drawn by hue is described.

An ultrasound diagnostic apparatus 1 according to the second embodiment has the same configuration as that of the ultrasound diagnostic apparatus 1 exemplified in FIG. 1, but a part of the processing of the image generation function 142 and the combining function 143 is different. In the second embodiment, the difference from the first embodiment is mainly described, and a description of the same functions as those described in the first embodiment is omitted.

The image generation function 142 according to the second embodiment generates an elasticity image in which a difference in value in elasticity information is represented by at least a difference in hue and a blood flow image in which a difference in value in blood flow information is represented by a difference other than the difference in hue.

Figure 8A:
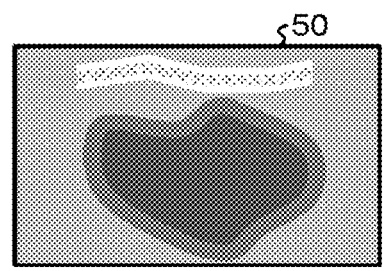
FIG. 8A is a diagram for describing processing of an image generation function according to a second embodiment.
Figure 8B:
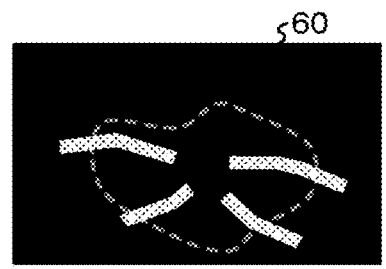
FIG. 8B is a diagram for describing processing of the image generation function according to the second embodiment.

FIG. 8A and FIG. 8B are diagrams for describing processing of the image generation function 142 according to the second embodiment. FIG. 8A exemplifies an elasticity image generated by the image generation function 142. FIG. 8B exemplifies a blood flow image generated by the image generation function 142. Note that, the broken line in FIG. 8B shows the positional correspondence with the elasticity image of FIG. 8A, and is not displayed on the blood flow image in practice.

As illustrated in FIG. 8A, for example, the image generation function 142 converts a scanning mode of the elasticity information generated by the signal processing circuitry 130 into a display data format. Then, the image generation function 142 allocates each pixel in the converted data with a color corresponding to its pixel value in accordance with an elasticity image color look-up table (LUT). In the elasticity image color LUT, colors including hues (color temperatures) that differ depending on pixel values are set. Specifically, the image generation function 142 allocates each pixel with gradation that continuously changes in the order of "blue-green-red" in accordance with a change in hardness (strain) from a small value (soft) to a large value (hard), to thereby generate an elasticity image 50.

As illustrated in FIG. 88B, the image generation function 142 converts a scanning mode of the blood flow information generated by the signal processing circuitry 130 into a display data format. Then, the image generation function 142 allocates each pixel in the converted data with the gray scale corresponding to its pixel value in accordance with a blood flow image color LUT. Specifically, when the power of the blood flow is imaged as blood flow information, the image generation function 142 allocates each pixel with the gray scale whose luminance changes in accordance with a change in power from a small value (soft) to a large value (hard), to thereby generate a blood flow image 60.

The combining function 143 according to the second embodiment generates a combined image 70 by superimposing the elasticity image 50 on the blood flow image 60.

Figure 9:
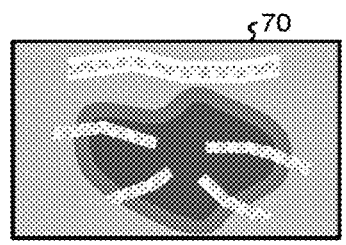
FIG. 9 is a diagram for describing processing of a combining function according to the second embodiment.

FIG. 9 is a diagram for describing processing of the combining function 143 according to the second embodiment. As illustrated in FIG. 9, for example, the combining function 143 extracts a blood flow region from the blood flow image 60, and fills regions other than the extracted blood flow region with a predetermined luminance (for example, black). Then, the combining function 143 generates the combined image 70 by superimposing the elasticity image 50 on the blood flow image 60, in which the regions other than the blood flow region are filled with color, with a predetermined transparency (such a transparency that the underlying blood flow image 60 is viewable). In this manner, the combined image 70 having the clear blood flow region is obtained.

Note that, the combining function 143 may generate the combined image 70 by clipping out the blood flow region from the blood flow image 60 and superimposing the clipped blood flow region on the elasticity image 50. In the case where monochrome color gradation is allocated to the blood flow image 60, it is preferred that the color gradation be not close to the hue of the color LUT of the elasticity image 50.

As described above, the ultrasound diagnostic apparatus 1 according to the second embodiment generates the combined image 70 by combining the blood flow image 60 drawn by monochrome color gradation and the elasticity image 50 drawn by hue. Consequently, the ultrasound diagnostic apparatus 1 according to the second embodiment can generate a combined image in which the blood flow and the tissue property are appropriately represented.

Third Embodiment

In the above-mentioned first and second embodiments, the case where an elasticity image is generated by TDI is described, but the embodiments are not limited thereto. For example, the ultrasound diagnostic apparatus 1 may generate an elasticity image based on correlation calculation between adjacent frames. In a third embodiment, the case where the ultrasound diagnostic apparatus 1 generates an elasticity image based on correlation calculation between adjacent frames is described.

An ultrasound diagnostic apparatus 1 according to the third embodiment has the same configuration as that of the ultrasound diagnostic apparatus 1 exemplified in FIG. 1, but a part of the processing of the signal processing circuitry 130 is different. In the third embodiment, the difference from the first embodiment is mainly described, and a description of the same functions as those described in the first embodiment is omitted.

Figure 10:
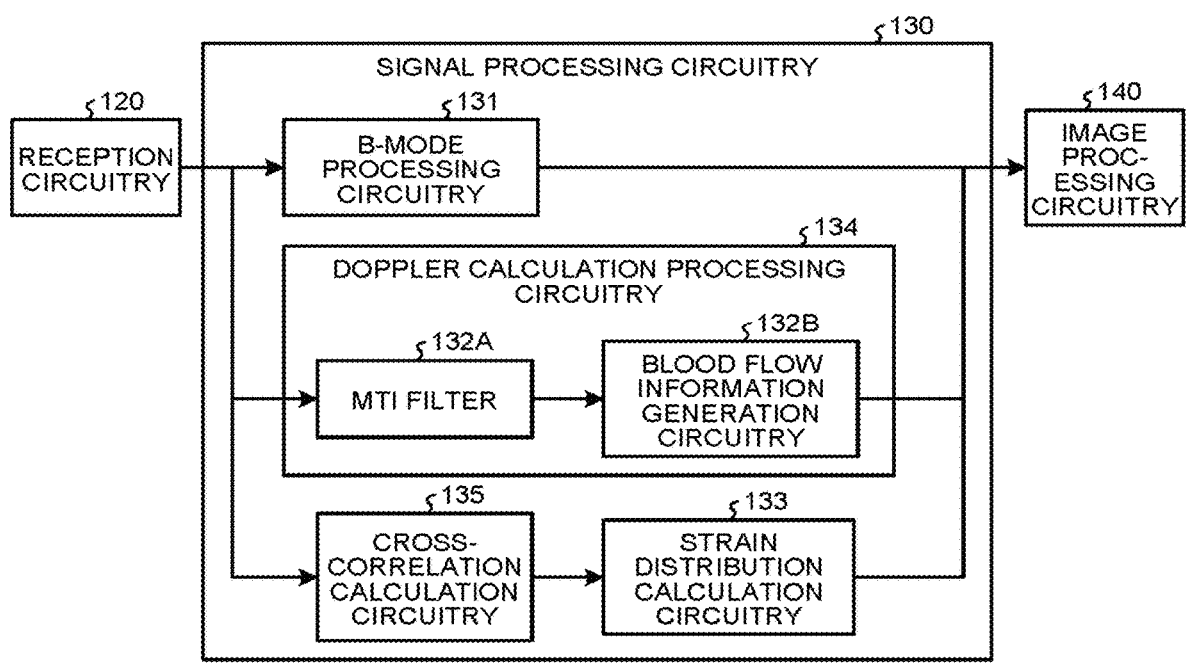
FIG. 10 is a block diagram illustrating a configuration example of a signal processing circuit according to a third embodiment.

FIG. 10 is a block diagram illustrating a configuration example of a signal processing circuitry 130 according to the third embodiment. As illustrated in FIG. 10, the signal processing circuitry 130 includes B-mode processing circuitry 131, strain distribution calculation circuitry 133, Doppler calculation processing circuitry 134, and cross-correlation calculation circuitry 135. Note that, the B-mode processing circuitry 131 and the strain distribution calculation circuitry 133 are the same as the B-mode processing circuitry 131 and the strain distribution calculation circuitry 133 illustrated in FIG. 2, and hence a description thereof is omitted.

The Doppler calculation processing circuitry 134 includes the MTI filter 132A and the blood flow information generation circuitry 132B similarly to the Doppler calculation processing circuitry 132 exemplified in FIG. 2, but does not include the tissue movement velocity generation circuitry 132C, which is different. The MTI filter 132A and the blood flow information generation circuitry 132B are the same as the MTI filter 132A and the blood flow information generation circuitry 132B illustrated in FIG. 2, and hence a description thereof is omitted. In other words, the Doppler calculation processing circuitry 134 generates blood flow information through substantially the same processing as that of the Doppler calculation processing circuitry 132.

The cross-correlation calculation circuitry 135 generates tissue displacement information based on reflected wave data transmitted from the reception circuitry 120. The tissue displacement information is information to be input to the strain distribution calculation circuitry 133 configured to generate elasticity information.

Figure 11:
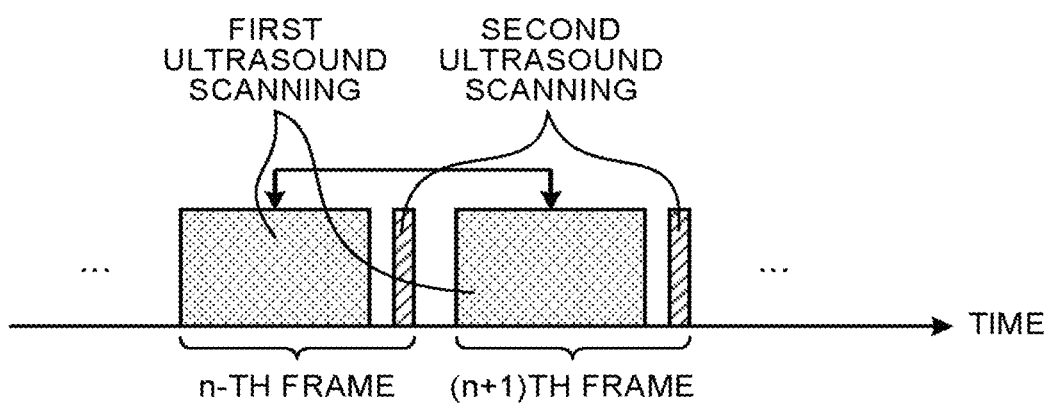
FIG. 11 is a diagram for describing processing of a cross-correlation calculation circuit according to the third embodiment.

FIG. 11 is a diagram for describing processing of the cross-correlation calculation circuitry 135 according to the third embodiment. FIG. 11 exemplifies the same scan sequence as in FIG. 3. In other words, also in the third embodiment, the same scan sequence as the scan sequence in the first embodiment illustrated in FIG. 3 is executed.

The cross-correlation calculation circuitry 135 calculates a cross-correlation (or phase difference) of IQ signals (or RF signals) at the same position between adjacent frames, to thereby generate tissue displacement information representing a displacement of the tissue between the frames. Specifically, as indicated by the arrows in FIG. 11, the cross-correlation calculation circuitry 135 acquires IQ signals from first ultrasound scanning that is executed for each of the n-th frame and the (n+1)th frame. Then, the cross-correlation calculation circuitry 135 calculates a cross-correlation of IQ signals at the same position between the n-th frame and the (n+1)th frame, to thereby generate tissue displacement information between these frames. Then, the strain distribution calculation circuitry 133 takes the spatial derivative of the displacement of the tissue generated by the cross-correlation calculation circuitry 135, to thereby calculate elasticity information.

As described above, the Doppler calculation processing circuitry 134 can generate elasticity information (tissue property information) based on correlation calculation between received data pieces for adjacent frames. Note that, elasticity information (elasticity image) generated with use of the received data pieces for the n-th frame and the (n+1)th frame is displayed at the same time as a tomographic image and a blood flow image generated from the received data for the n-th frame or the (n+1)th frame. Consequently, the pieces of information at substantially the same time point and in substantially the same cross-section can be displayed at the same time.

Fourth Embodiment

In a fourth embodiment, a description is given of the case where ultrasound scanning is executed at a frame rate that is higher than those in the above-mentioned first to third embodiments.

For example, in order to improve performance of the MTI filter 132A in the configuration described in the first to third embodiments, it is preferred to increase a data sequence (packets) of reflected wave data obtained by ultrasound scanning for each frame. In this case, however, the frame rate decreases along with the increase in packet size. In the fourth embodiment, a configuration for increasing the frame rate is described.

The control circuitry 170 according to the fourth embodiment collects blood flow information (and elasticity information) in such a manner that ultrasound scanning for the scanning range is repeatedly executed in a scanning form that can collect reflected wave data at the same position over a plurality of frames. Furthermore, the control circuitry 170 collects tomographic information in such a manner that partial ultrasound scanning for divided scanning ranges is executed over a plurality of frames while switching the divided region. Specifically, the control circuitry 170 executes partial ultrasound scanning with divided scanning ranges while switching the divided regions in the course of ultrasound scanning of blood flow information that is repeatedly executed over a plurality of frames.

Figure 12:
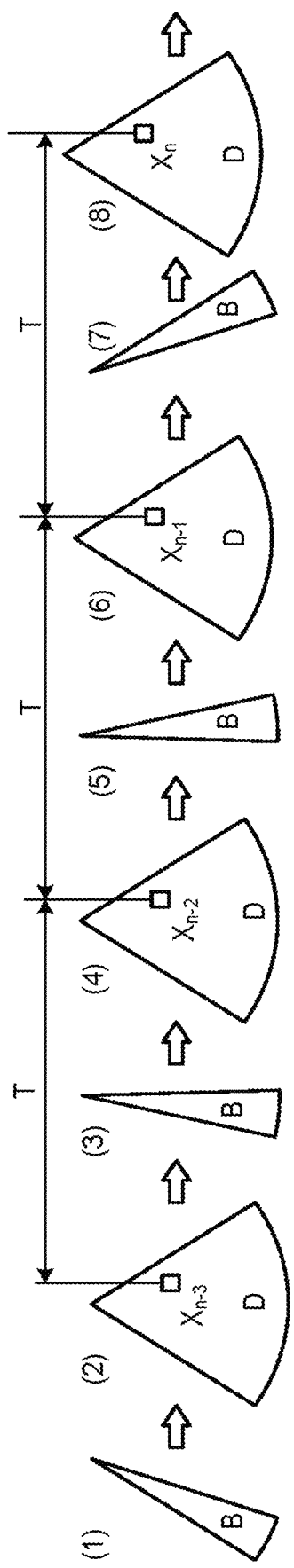
FIG. 12 is a diagram for describing processing of a control circuit according to a fourth embodiment.

FIG. 12 is a diagram for describing processing of the control circuitry 170 according to the fourth embodiment. "B" illustrated in FIG. 12 indicates a range where ultrasound scanning is performed under transmission and reception conditions of the B-mode. Specifically, the range where the B-mode ultrasound scanning is performed is divided into four divided regions (first divided region to fourth divided region). Furthermore, "D" illustrated in FIG. 12 indicates a range where ultrasound scanning is performed under transmission and reception conditions of the color Doppler mode. For example, "D" illustrated in FIG. 12 is the range where ultrasound scanning is performed at a high rate as described above. Specifically, ultrasound scanning exemplified in FIG. 12 is performed such that ultrasound waves are transmitted and received once on each scanning line, unlike the commonly used color Doppler imaging where ultrasound waves are transmitted a plurality of times in the same direction and reflected waves are received a plurality of times. The control circuitry 170 executes, as color Doppler-mode ultrasound scanning, ultrasound scanning that is based on a method of transmitting and receiving ultrasound waves once for each of a plurality of scanning lines forming the scanning range, and acquiring blood flow information with use of reflected waves for a plurality of frames (high frame rate method).

First, the control circuitry 170 executes B-mode ultrasound scanning for the first divided region (see (1) in FIG. 12), and executes color Doppler-mode ultrasound scanning for a scanning range of one frame (see (2) in FIG. 12). Then, the control circuitry 170 executes B-mode ultrasound scanning for the first divided region (see (3) in FIG. 12), and executes color Doppler-mode ultrasound scanning for a scanning range of one frame (see (4) in FIG. 12). Then, the control circuitry 170 executes B-mode ultrasound scanning for the first divided region (see (5) in FIG. 12), and executes color Doppler-mode ultrasound scanning for a scanning range of one frame (see (6) in FIG. 12). Then, the control circuitry 170 executes B-mode ultrasound scanning for the first divided region (see (7) in FIG. 12), and executes color Doppler-mode ultrasound scanning for a scanning range of one frame (see (8) in FIG. 12).

As exemplified in FIG. 12, the control circuitry 170 controls the intervals for color Doppler-mode ultrasound scanning to be uniform. In other words, the "point X" on the scanning range is scanned once by the ultrasound scanning of (2), (4), (6), and (8) in FIG. 12, and the scanning intervals therefor are controlled to be constant "T". Specifically, the control circuitry 170 controls the intervals for color Doppler-mode ultrasound scanning to be uniform by setting the time necessary for each divisional scanning performed in B-mode ultrasound scanning to be equal to each other. For example, the control circuitry 170 controls the time necessary for divisional scanning for B-mode ultrasound scanning performed at (1), (3), (5), and (7) in FIG. 12 to be the same time without exception. The control circuitry 170 controls the sizes of the divided regions, the number of scanning lines, and the densities and depths of the scanning lines to be equal. For example, when the number of scanning lines is the same, the time necessary for each divisional scanning for B-mode ultrasound scanning is the same. The signal processing circuitry 130 performs processing such as correlation calculation on a data sequence at the same position among the frames D ("$X_{n-3}, X_{n-2}, X_{n-1}, X_n, \ldots$" illustrated in FIG. 12), and outputs blood flow information and elasticity information at the "point X".

As described above, the ultrasound diagnostic apparatus 1 according to the fourth embodiment can execute ultrasound scanning at a high frame rate. Consequently, the ultrasound diagnostic apparatus 1 can generate blood flow information and elasticity information to be converted into an image and displayed in a frame period for forming a single tomographic image, thus enabling the pieces of information at substantially the same time point and in substantially the same cross-section to be displayed at the same time.

Other Embodiments

In addition to the above-mentioned embodiments, various different embodiments may be implemented.

Case where morphologic image, blood flow image, and elasticity image are generated by different ultrasound scanning In the above-mentioned embodiments, for example, the case where a blood flow image and an elasticity image are generated by the same ultrasound scanning is described, but the embodiments are not limited thereto. For example, a morphologic image, a blood flow image, and an elasticity image may be generated by different ultrasound scanning.

Figure 13:
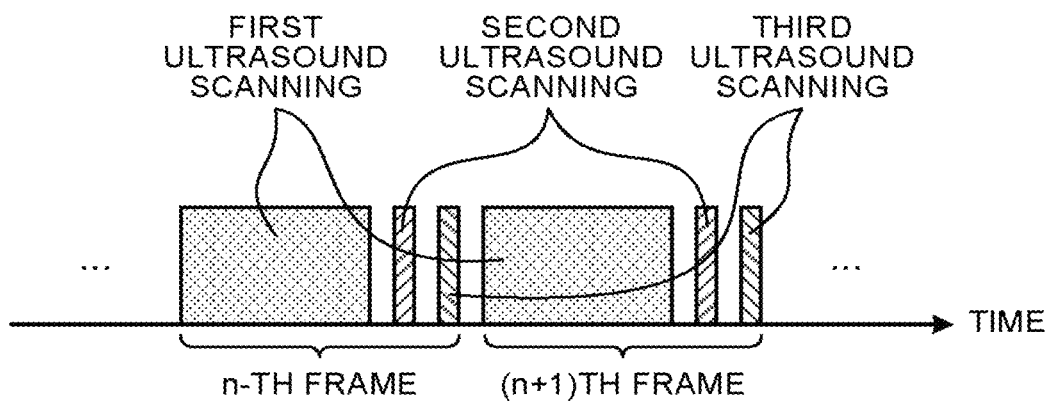
FIG. 13 is a diagram illustrating an exemplary scan sequence according to other embodiments.

FIG. 13 is a diagram illustrating an exemplary scan sequence according to other embodiments. In FIG. 13, the horizontal axis corresponds to time. Ultrasound scanning for each frame includes first ultrasound scanning, second ultrasound scanning, and third ultrasound scanning. The first ultrasound scanning and the second ultrasound scanning are the same as those illustrated in FIG. 3. In other words, a blood flow image (blood flow information) is generated from the first ultrasound scanning, and a morphologic image (morphologic information) is generated from the second ultrasound scanning.

The third ultrasound scanning is executed in order to generate an elasticity image (elasticity information). In this case, for example, the signal processing circuitry 130 calculates elasticity information by generating tissue movement velocity information by TDI from reflected wave data obtained by the third ultrasound scanning. Note that, without being limited thereto, the signal processing circuitry 130 may generate an elasticity image based on correlation calculation between adjacent frames.

Application of Shear Wave Elastography

In the above-mentioned embodiments, an elasticity image is generated by strain elastography for imaging a strain that is caused by minute vibration generated by an action of bringing the ultrasound probe 101 into contact with the body surface, but the generation method is not limited thereto. For example, shear wave elastography may be applied, which applies acoustic radiation force (push pulse) to a biological tissue from the body surface so as to generate a displacement based on shear waves, and observes the displacement at each point within a scanning cross-section with time, to thereby determine the elastic modulus based on a propagating velocity of the shear waves.

Referring to FIG. 13, ultrasound scanning applied with shear wave elastography is described. In this case, the first ultrasound scanning and the second ultrasound scanning are the same as those in the above description. In other words, a blood flow image (blood flow information) is generated from the first ultrasound scanning, and a morphologic image (morphologic information) is generated from the second ultrasound scanning.

Here, the third ultrasound scanning is ultrasound scanning for generating an elasticity image (elasticity information) through shear wave elastography. Note that, in the shear wave elastography, shear waves generated by single push pulse transmission are attenuated in the course of propagation, and hence a single region of interest is divided into a plurality of small regions for scanning. Referring to FIG. 13, a description is given of the case where the region of interest is divided into three small regions for scanning, and elasticity images in the three small regions are combined to obtain a single elasticity image corresponding to the region of interest. For the sake of description, the three small regions are denoted by "small regions A, B, and C".

Specifically, at the n-th frame, a blood flow image is generated from the first ultrasound scanning, a morphologic image is generated from the second ultrasound scanning, and an elasticity image in the small region A is generated from the third ultrasound scanning. Subsequently, at the (n+1)th frame, a blood flow image is generated from the first ultrasound scanning, a morphologic image is generated from the second ultrasound scanning, and an elasticity image in the small region B is generated from the third ultrasound scanning. Then, at the (n+2)th frame, a blood flow image is generated from the first ultrasound scanning, a morphologic image is generated from the second ultrasound scanning, and an elasticity image in the small region C is generated from the third ultrasound scanning. By combining the elasticity images in the small regions A, B, and C, a single elasticity image corresponding to the region of interest can be generated. In other words, the elasticity image generated by shear wave elastography is low in frame rate as compared with the blood flow image and the morphologic image depending on the number of small regions. Note that, the elasticity image generated by shear wave elastography can be used for the generation and display of combined image data similarly to the elasticity image generated by strain elastography described in the above-mentioned embodiments, except that the frame rate is lower.

Other Tissue Property Images

Other images than the above-mentioned elasticity image, such as an attenuation image, an acoustic structure quantification (ASQ) mode image, and a microcalcification emphasized image are also applicable as tissue property images.

As used herein, the attenuation image refers to an image obtained by converting how ultrasound waves propagating through a living body are attenuated into an image. For example, the amount of attenuation of ultrasound waves is estimated from signal intensity of a reflected wave signal that is obtained when ultrasound waves at a predetermined frequency are transmitted and received.

The ASQ-mode image refers to an image obtained by determining the degree of deviance (variance) of signal amplitude distribution of received signals from a Rayleigh distribution through statistical filtering, and converting the determined variance into an image.

The microcalcification emphasized image refers to an image obtained by extracting, from a B-mode image, microcalcifications occurring in a tissue to be observed, and converting the extracted microcalcifications into an image.

When the above-mentioned attenuation image, ASQ-mode image, or microcalcification emphasized image is combined with a blood flow image as a tissue property image, it is preferred that the blood flow image be represented by a difference in hue and the tissue property image be represented by a difference other than the difference in hue.

Medical Image Processing Device

Furthermore, the processing described in the above-mentioned embodiments may be executed by a medical image processing apparatus.

Figure 14:
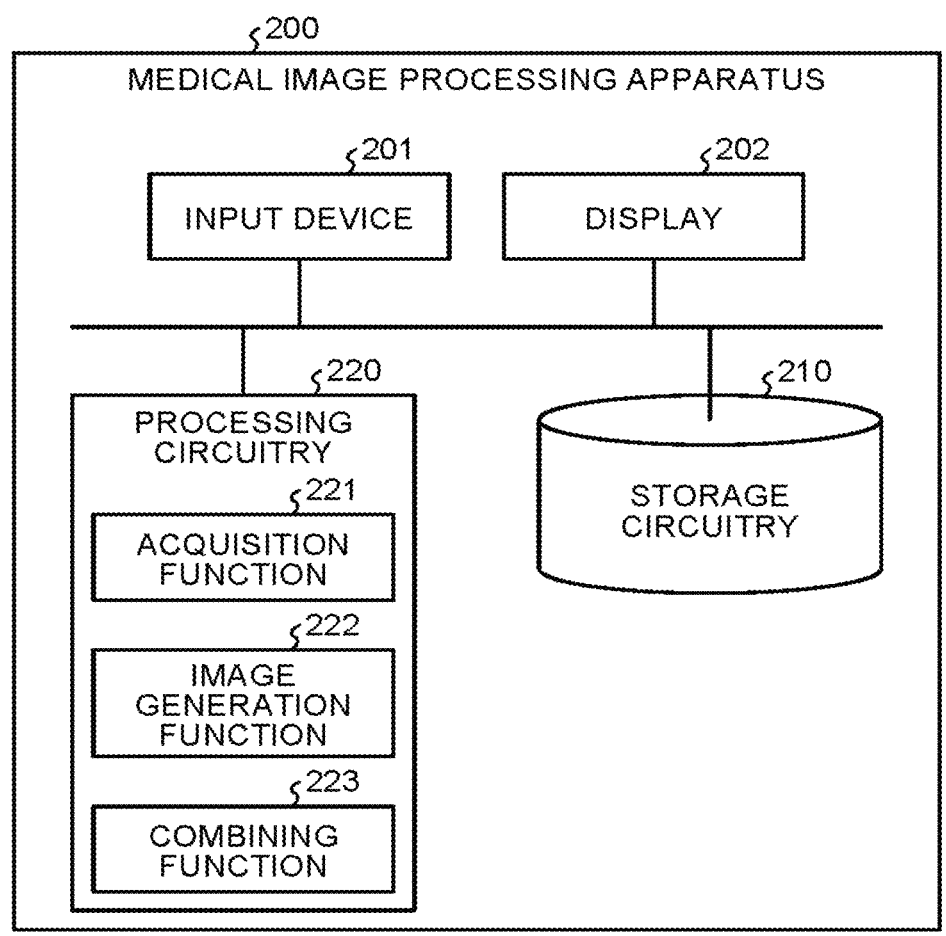
FIG. 14 is a block diagram illustrating a configuration example of a medical image processing apparatus according to other embodiments.

FIG. 14 is a block diagram illustrating a configuration example of a medical image processing apparatus according to other embodiments. As illustrated in FIG. 14, a medical image processing apparatus 200 includes an input device 201, a display 202, storage circuitry 210, and processing circuitry 220.

The input device 201 includes a mouse, a keyboard, a button, a panel switch, a touch command screen, a foot switch, a trackball, a joystick, or any other device. The input device 201 receives various kinds of setting requests from an operator of the medical image processing apparatus 200, and transfers various kinds of received setting requests to each processing unit.

The display 202 displays a GUI, which is used for the operator of the medical image processing apparatus 200 to input various kinds of setting requests with use of the input device 201, and displays information generated by the medical image processing apparatus 200 and any other information.

The storage circuitry 210 is a nonvolatile storage device as represented by a semiconductor memory element such as a flash memory, a hard disk, and an optical disc.

The processing circuitry 220 is an integrated circuit such as an ASIC and an FPGA, or an electronic circuit such as a CPU and an MPU. The processing circuitry 220 controls the overall processing of the medical image processing apparatus 200.

Furthermore, the processing circuitry 220 executes an acquisition function 221, an image generation function 222, and a combining function 223. The acquisition function 221, the image generation function 222, and the combining function 223 have the same functions as the acquisition function 141, the image generation function 142, and the combining function 143 described in the above-mentioned embodiments, respectively.

Specifically, the acquisition function 221 acquires blood flow information and tissue property information. Based on the blood flow information acquired by the acquisition function 221, the image generation function 222 generates a blood flow image 20 in which a difference in value in the blood flow information including a value that is based on the blood flow at each position within the subject is represented by at least a difference in hue. Furthermore, the image generation function 222 generates, from the tissue property information acquired by the acquisition function 221, an elasticity image 10 in which a difference in value in the tissue property information that includes a value based on a tissue property at each position within the subject is represented by a difference other than the difference in hue. Then, the image generation function 222 stores the generated blood flow image 20 and elasticity image 10 in the storage circuitry 210. Then, the combining function 223 combines the blood flow image 20 and the elasticity image 10 to generate a combined image 30.

Note that, the medical image processing apparatus 200 may acquire the already-generated blood flow image 20 and elasticity image 10 from a modality, and combine the acquired images. In this case, the acquisition function 221 acquires each of the blood flow image 20 and the elasticity image 10 by modality, and stores the acquired blood flow image 20 and elasticity image 10 in the storage circuitry 210.

Then, the combining function 223 generates the combined image 30 by combining the blood flow image 20 and the elasticity image 10.

Furthermore, although the case of generating the combined image 30 by combining the blood flow image 20 and the elasticity image 10 is described with reference to FIG. 14, a combined image 70 may be generated by combining a blood flow image 60 and an elasticity image 50.

Furthermore, each component of each device is conceptually illustrated based on its function, and is not necessarily required to physically configured as illustrated. In other words, a specific mode for dispersion and integration of the devices is not limited to the illustrated one, and all or part of the devices can be functionally or physically dispersed and integrated in arbitrary units depending on various kinds of loads, usage conditions, and any other parameter. In addition, all or any part of each processing function executed by each device may be implemented by a CPU and a program analyzed and executed by the CPU, or implemented as hardware by wired logic.

Furthermore, among the processing contents described in the above-mentioned embodiments, all or part of the processing that is described as being automatically executed can also be manually executed, or all or part of the processing that is described as being manually executed can also be automatically executed by a known method. In addition, the processing procedures, the control procedures, the specific names, and the information including various kinds of data and parameters described herein and illustrated in the accompanying drawings can be arbitrarily changed unless otherwise specified.

Furthermore, the medical image processing method described in the above-mentioned embodiment can be implemented by a personal computer or a workstation computer executing a medical image processing program prepared in advance. The medical image processing program can be distributed via a network such as the Internet. Furthermore, the medical image processing program can be recorded in a computer-readable recording medium, such as a hard disk, a flexible disk (FD), a CD-ROM, an MO, and a DVD, and executed by a computer reading the program from the recording medium.

According to at least one of the embodiments described above, a combined image in which a blood flow and a tissue property are appropriately represented can be generated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising image processing circuitry configured to:
   acquire, based on a result of first ultrasound scanning performed on a subject, blood flow information including a power value of a blood flow at each position within the subject;
   acquire a blood flow image which represents a blood flow region where the power value is equal to or larger than a threshold value, based on the acquired blood flow information;

acquire, based on a result of second ultrasound scanning performed on the subject, tissue property information including a value that represents a tissue property at each position within the subject;

acquire a tissue property image based on the acquired tissue property information, the tissue property image being acquired using each of two or more divisional regions;

acquire, based on a result of third ultrasound scanning performed on the subject, a morphologic image representing a morphology of a structure within the subject;

generate a combined image by superimposing the tissue property image acquired using the two or more divisional regions, on which the acquired single blood flow image is superimposed, on the acquired single morphologic image, wherein the blood flow image is a top layer image in the combined image, the tissue property image is a middle layer image in the combined image, and the morphologic image is a bottom layer image in the combined image, and display the generated combined image, wherein the first ultrasound scanning, the second ultrasound scanning, and the third ultrasound scanning are performed in a time-division manner during a single scanning sequence, a frame rate of the tissue property image used in the combined image is lower than a frame rate of the blood flow image and a frame rate of the acquired morphologic image used in the combined image, and the tissue property image is any one of an attenuation image, an acoustic structure quantification (ASQ) mode image, a degree of deviance (variance) of signal amplitude distribution of received signals from a Rayleigh distribution through statistical filtering, and a micro calcification emphasized image.

2. An ultrasound diagnostic apparatus, comprising image processing circuitry configured to:

acquire, based on a result of first ultrasound scanning performed on a subject, blood flow information including a power value of a blood flow at each position within the subject;

acquire a blood flow image which represents a blood flow region where the power value is equal to or larger than a threshold value, based on the acquired blood flow information;

acquire, based on a result of second ultrasound scanning performed on the subject, tissue property information including a value that represents a tissue property at each position within the subject;

acquire a tissue property image based on the acquired tissue property information, the tissue property image being acquired using each two or more divisional regions;

acquire, based on a result of third ultrasound scanning performed on the subject, a morphologic image representing a morphology of a structure within the subject;

generate a combined image by superimposing the tissue property image acquired using the two or more divisional regions, on which the acquired single blood flow image is superimposed, on the acquired single morphologic image, wherein the blood flow image is a top layer image in the combined image, the tissue property image is a middle layer image in the combined image, the morphologic image is a bottom layer image in the combined image; and display the generated combined image, wherein the first ultrasound scanning, the second ultrasound scanning, and the third ultrasound scanning are performed in a time-division manner during a single scanning sequence, the first ultrasound scanning and the third ultrasound scanning are performed multiple times in the single scanning sequence for displaying the combined image, and the tissue property image is any one of an attenuation image, an acoustic structure quantification (ASQ) mode image, a degree of deviance (variance) of signal amplitude distribution of received signals from a Rayleigh distribution through statistical filtering, and a micro calcification emphasized image.

3. The ultrasound diagnostic apparatus according to claim 1, wherein a difference in value in the tissue property information is represented by any one of a difference in hue, a combination of a difference in hue and a difference in lightness, a combination of a difference in hue and a difference in chroma, and a combination of a difference in hue, a difference in lightness, and a difference in chroma, and a difference in value in the blood flow information is represented by any one of a difference in lightness, a difference in chroma, and a combination of a difference in lightness and a difference in chroma.

4. The ultrasound diagnostic apparatus according to claim 1, wherein the image processing circuitry generates the combined image by superimposing the acquired blood flow image and the acquired tissue property image on the acquired morphologic image in a non-transparent manner.

5. The ultrasound diagnostic apparatus according to claim 4, wherein the image processing circuitry displays the morphologic image on the display so that the morphologic image and the combined image are displayed side by side.

6. The ultrasound diagnostic apparatus according to claim 1, wherein the result of the second ultrasound scanning and the result of the first ultrasound scanning are included in a same received data sequence, and the image processing circuitry is configured to:

apply clutter removal filtering to the received data sequence for removing a clutter component that is obtained by a plurality of times of ultrasound transmission and reception performed for the same position, and acquire the blood flow information from the received data sequence after the application of the clutter removal filtering; and acquire the tissue property information from the received data sequence before the application of the clutter removal filtering.

7. The ultrasound diagnostic apparatus according to claim 6, wherein a plurality of the first ultrasound scanning is executed repeatedly during the single scanning sequence, and each of data sequences acquired in the received data in each of the repeatedly executed first ultrasound scanning is converted into the blood flow image in a frame period.

8. The ultrasound diagnostic apparatus according to claim 1, wherein the result of the second ultrasound scanning includes a plurality of the results of the first ultrasound scanning, and the tissue property information is acquired based on correlation calculation between a plurality of pieces of the result of the second ultrasound scanning received data that include received data used to acquire the blood flow information.

9. The ultrasound diagnostic apparatus according to claim 1, wherein the second ultrasound scanning is performed after the third ultrasound scanning during the single scanning sequence.

10. The ultrasound diagnostic apparatus according to claim 1, wherein the first ultrasound scanning and the second ultrasound scanning are not executed while the third ultrasound scanning is executed in each of the single scanning sequence.

11. The ultrasound diagnostic apparatus according to claim 1, wherein the first ultrasound scanning and the third ultrasound scanning are performed multiple times in the single scanning sequence for displaying the combined image.

12. The ultrasound diagnostic apparatus according to claim 1, wherein the image processing circuitry generates the tissue property information based on correlation calculation between received data for adjacent frames.

13. An ultrasound diagnostic apparatus, comprising image processing circuitry configured to:
 acquire, based on a result of first ultrasound scanning performed on a subject, blood flow information including a power value of a blood flow at each position within the subject;
 acquire a blood flow image which represents a blood flow region where the power value is equal to or larger than a threshold value, based on the acquired blood flow information;
 acquire, based on a result of second ultrasound scanning performed on the subject, tissue property information including a value that represents a tissue property at each position within the subject;
 acquire a tissue property image based on the acquired tissue property information, the tissue property image being acquired using each two or more divisional regions;
 acquire, based on a result of third ultrasound scanning performed on the subject, a morphologic image representing a morphology of a structure within the subject;
 generate a combined image by superimposing the tissue property image acquired using the two or more divisional regions, on which the acquired single blood flow image is superimposed, on the acquired single morphologic image, wherein
  the blood flow image is a top layer image in the combined image,
  the tissue property image is a middle layer image in the combined image,
  the morphologic image is a bottom layer image in the combined image; and
 display the generated combined image, wherein
  the first ultrasound scanning, the second ultrasound scanning, and the third ultrasound scanning are performed in a time-division manner during a single scanning sequence,
  the first ultrasound scanning and the third ultrasound scanning are performed multiple times in the single scanning sequence for displaying the combined image, and
  the tissue property image is any one of an attenuation image, an acoustic structure quantification (ASQ) mode image, a degree of deviance (variance) of signal amplitude distribution of received signals from a Rayleigh distribution through statistical filtering, and a micro calcification emphasized image.

14. The ultrasound diagnostic apparatus according to claim 13, wherein the image processing circuitry generates the combined image by superimposing the acquired blood flow image and the acquired tissue property image on the acquired morphologic image in a non-transparent manner.

15. The ultrasound diagnostic apparatus according to claim 13, wherein the result of the second ultrasound scanning and the result of the first ultrasound scanning are included in a same received data sequence, and the image processing circuitry is configured to:
 apply clutter removal filtering to the received data sequence for removing a clutter component that is obtained by a plurality of times of ultrasound transmission and reception performed for the same position, and
 acquire the blood flow information from the received data sequence after the application of the clutter removal filtering; and
 acquire the tissue property information from the received data sequence before the application of the clutter removal filtering.

16. The ultrasound diagnostic apparatus according to claim 15, wherein a plurality of the first ultrasound scanning is executed repeatedly during the single scanning sequence, and each of data sequences acquired in the received data in each of the repeatedly executed first ultrasound scanning is converted into the blood flow image in a frame period.

17. The ultrasound diagnostic apparatus according to claim 13, wherein the result of the second ultrasound scanning includes a plurality of the results of the first ultrasound scanning, and the tissue property information is acquired based on correlation calculation between a plurality of pieces of the result of the second ultrasound scanning received data that include received data used to acquire the blood flow information.

18. The ultrasound diagnostic apparatus according to claim 13, wherein a difference in value in the blood flow information is represented by any one of a difference in hue, a combination of a difference in hue and a difference in lightness, a combination of a difference in hue and a difference in chroma, and a combination of a difference in hue, a difference in lightness, and a difference in aroma, and a difference in value in the tissue property information is represented by any one of a difference in lightness, a difference in chroma, and a combination of a difference in lightness and a difference in chroma.

19. The ultrasound diagnostic apparatus according to claim 13, wherein a difference in value in the tissue property information is represented by any one of a difference in hue, a combination of a difference in hue and a difference in lightness, a combination of a difference in hue and a difference in chroma, and a combination of a difference in hue, a difference in lightness, and a difference in chroma, and a difference in value in the blood flow information is represented by any one of a difference in lightness, a difference in chroma, and a combination of a difference in lightness and a difference in chroma.

20. The ultrasound diagnostic apparatus according to claim 13, wherein the second ultrasound scanning is performed after the third ultrasound scanning during the single scanning sequence.

21. The ultrasound diagnostic apparatus according to claim 13, wherein the first ultrasound scanning and the second ultrasound scanning are not executed while the third ultrasound scanning is executed in each of the single scanning sequence.

* * * * *